(12) United States Patent
Marti

(10) Patent No.: US 12,042,419 B2
(45) Date of Patent: Jul. 23, 2024

(54) SHOULDER REHABILITATION BRACE

(71) Applicant: Eduardo Marti, Weston, FL (US)

(72) Inventor: Eduardo Marti, Weston, FL (US)

( * ) Notice: Subject to any disclaimer, the term of this patent is extended or adjusted under 35 U.S.C. 154(b) by 454 days.

(21) Appl. No.: 16/726,817

(22) Filed: Dec. 24, 2019

(65) Prior Publication Data

US 2021/0038417 A1 Feb. 11, 2021

Related U.S. Application Data

(63) Continuation-in-part of application No. 16/537,558, filed on Aug. 10, 2019, now abandoned.

(51) Int. Cl.
*A61F 5/01* (2006.01)
*A61F 5/05* (2006.01)

(52) U.S. Cl.
CPC .............. *A61F 5/0193* (2013.01); *A61F 5/05* (2013.01)

(58) Field of Classification Search
CPC .... A61F 5/0113; A61F 5/0111; A61F 5/0102; A61F 5/0585; A61F 5/0127; A61F 5/3715; A61F 5/373; A61F 5/3723; A61F 5/3738; A61F 5/05; A61F 5/0193; A41D 13/0506; A47G 9/1045; A63B 21/4015; A63B 21/0552
See application file for complete search history.

(56) References Cited

U.S. PATENT DOCUMENTS

| | | | | |
|---|---|---|---|---|
| 3,739,772 A | * | 6/1973 | Ennis | A61F 13/041 602/4 |
| 4,188,944 A | * | 2/1980 | Augustyniak | A61F 5/05808 602/20 |
| 5,647,827 A | * | 7/1997 | Gutkowski | A63B 21/4025 482/122 |
| 2014/0276313 A1 | * | 9/2014 | Crafton | A61F 5/3715 602/26 |

OTHER PUBLICATIONS

Posture Corrector Brace Support, https://www.agonusa.com/product/posture-support-brace/.
Rotator Cuff Shoulder Sling Immobilizer, https://www.braceability.com/products/rotator-cuff-sling.
Donjoy Sully Shoulder Brace, https://www.betterbraces.com/saunders-sully-shoulder-support.

* cited by examiner

*Primary Examiner* — Ophelia A Hawthorne
(74) *Attorney, Agent, or Firm* — The Keys Law Firm PLLC

(57) ABSTRACT

A shoulder rehabilitation brace that operates to aid patients in rehabilitating their shoulder joint in an anatomically correct manner with the trapezius is locked down in order to prevent substantial upward shoulder shrug movements. Embodiments of the shoulder rehabilitation brace may include a shoulder strap and a thigh strap, with the shoulder strap using the thigh strap as an anchor while encircling a user's torso and engaging the user's shoulder to cause force to be exerted on the shoulder that prevents shoulder/scapular hiking and keeps the shoulder blade in retracted position in (Continued)

a manner that helps prevent potential shoulder impingement scenarios. In this regard, the shoulder rehabilitation brace is able to emulate the same "hand on trapezius area" function that therapists manually apply to patient rehabbing a shoulder condition in-clinic.

20 Claims, 9 Drawing Sheets

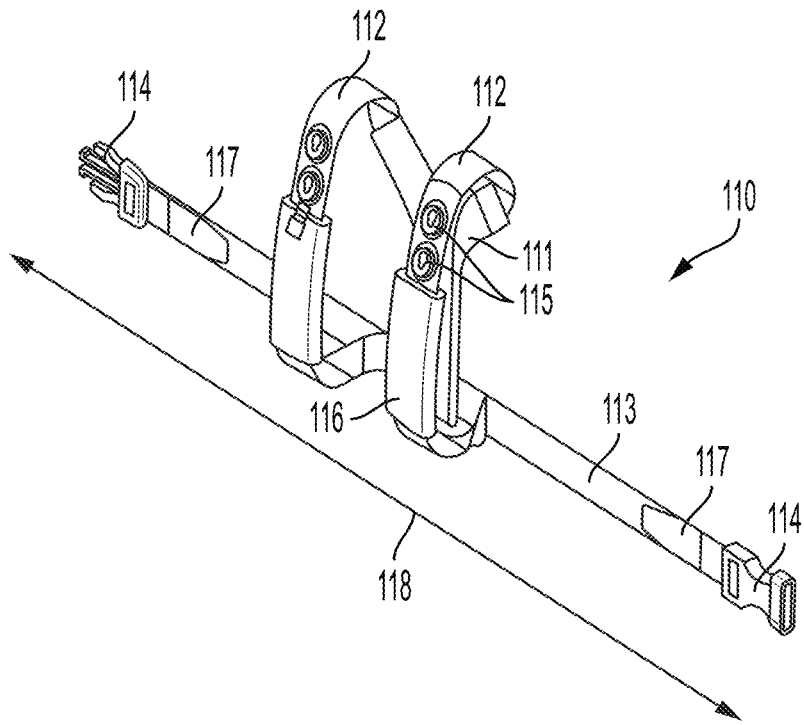
FIG. 3
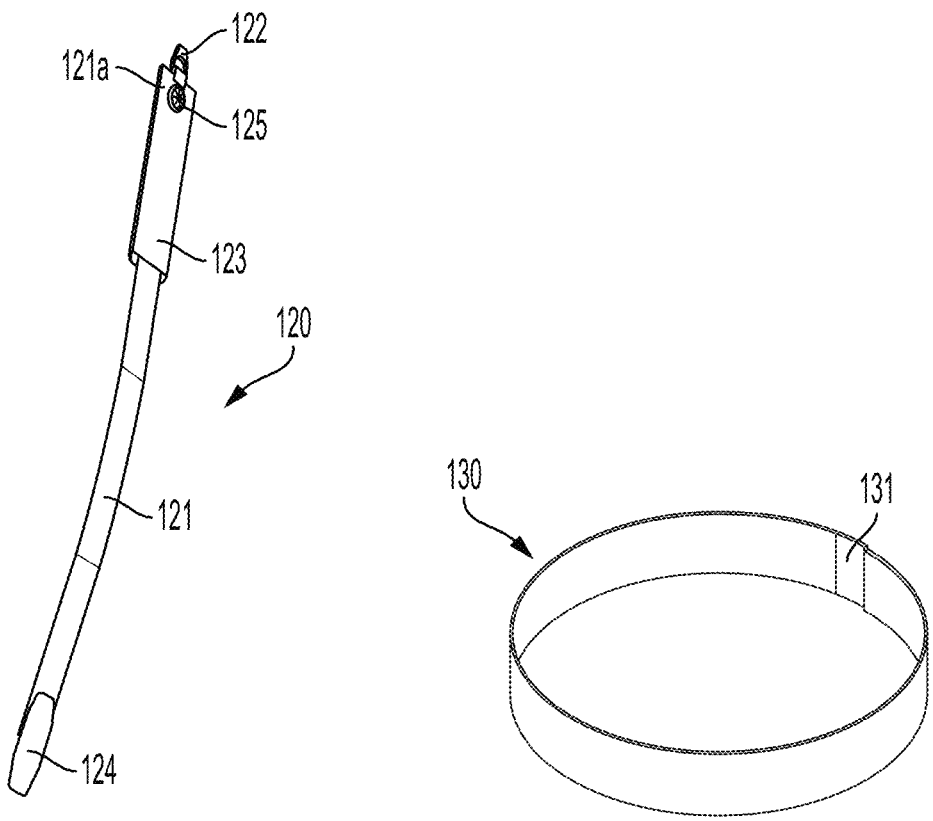
FIG. 4
FIG. 5

SHOULDER REHABILITATION BRACE

CROSS REFERENCE TO RELATED APPLICATIONS

This application is a continuation in part of, claims the benefit of, and incorporates by reference co-pending U.S. patent application Ser. No. 16/537,558 filed Aug. 10, 2019.

BACKGROUND OF THE INVENTION

Field of the Invention

This invention relates to a rehabilitation brace for use following injury to or surgery in the shoulder area that prevents a user from engaging in compensatory motion while moving their arm on during their physical therapy rehabilitation sessions.

Description of the Prior Art

The shoulder is the joint with the greatest amount of movement in the body. The shoulder is like a ball and socket, except that the socket is shallow which provides greater movement mechanics but less stability. Instability is a common problem and is the root of many shoulder injuries for not only young athletes but individuals of all ages. Indeed, while young athletes may often suffer from acute injuries, older individuals commonly suffer from the result of years and years of use and the muscular requirements to stabilize the shoulder. In any event, whether from injuries, overuse, or cumulative effects, shoulder conditions often become the leading cause of shoulder pain.

The shoulder moves in three axis of motion. One such motion is commonly referred to as abduction and adduction. Abduct means move away from the body and adduction toward the body. Another such motion is commonly referred to as internal and external. These can be envisioned from a starting point of one's elbow down to their side and their elbow bent at a ninety degree angle with hand facing forward. Moving the hand toward the center of your body with the elbow still at your side is internal rotation. Moving the hand away with elbow still at your side is external motion. Further, moving the elbow out to the side and while still moving the hand back and forth with it at your side is internal and external rotation in abduction. Yet another such motion is commonly referred to as transverse (or horizontal) rotation. This motion describes the act of going around the body center in a circular motion.

The shoulder girdle encompasses the junction between four major bones of the upper torso, namely, the sternum (breastbone), clavicle (collarbone), the scapula (shoulder blade), and the humorous (upper arm). The clavicle via the sternum serves as the bony attachment between the shoulder and the trunk itself. The other two bones of the shoulder are attached to the trunk by muscles and ligaments alone.

The outer end of the clavicle is attached to the scapula by the non-axial (i.e., limited to gliding movements) acromioclavicular joint (AC-joint). The humorous is attached to the scapula by the tri-axial (i.e., ability to move in three planes) glenohumeral joint. This joint is composed of the humeral head and the "socket" (glenoid fossa) of the scapula. The unique articulative relationship of these two joints and the third joint of the shoulder girdle, the non-axial sternoclavicular joint (located between the clavicle and the sternum) allows the shoulder to have an incredible range of motion.

The scapula, which is commonly referred to as the shoulder blade, is the triangular shaped bone on each side of a person's upper back. The socket of the shoulder joint is a part of the scapula. There are only three muscles that are responsible for enabling the movement of the shoulder blade. The first is the trapezius muscle, which implants into the collarbone and is responsible for movement of the shoulder and head. The second is the levator muscle, which is a small, thin muscle that arises from the vertebrae of the neck. A small tendon attaches the levator to the upper area of the shoulder blade. The levator is responsible for pulling up the scapula, which allows for the shrugging movement of the shoulders. The third is the rhomboideus, which actually comprises two muscles, the major and minor, located deep in the base of the shoulder blade. These rhomboideus muscles are responsible for raising the shoulder blade and moving it backwards. Separately, the muscles that move the shoulder forward come from the breast and upward movements are controlled by muscles located in the neck.

Normally the scapula will slide flat on the ribcage and rotate normally when an individual brings arms overhead. The scapula helps keep the shoulder centered in its socket and minimizes stress on the subacromial space. The scapula is not supposed to be the primary form of movement when the patient is engaged in shoulder movement that is not overhead.

Following shoulder injury or surgery in the shoulder area, however, it is often difficult and/or painful for an individual to properly move/use their arm/shoulder. As a result, the body compensates, and patients may rely too much on their scapula to help move their arm during rehabilitation (or "rehab"). This compensatory movement is called "shoulder hiking." Shoulder hiking can present many problems because following shoulder injury or surgery, it is imperative that the shoulder joint and/or shoulder capsule be rehabilitated properly to regain full range of motion and strength. If shoulder hiking takes place, it means the patient is essentially "cheating" their rehab efforts because in moving their arm, they are creating shoulder movement with the scapula rather than the shoulder joint. But since the shoulder joint should be driving all shoulder/arm movement that is not overhead, when patient relies on scapula to be the primary form of moving the shoulder (below head level), it will produce poor outcomes that will have short and long term consequences, both physical and financial.

Common problems that may require the use of measures which will prevent shoulder hiking during rehab include, but are not limited to: rotator cuff tears and tendinitis; shoulder bursitis; shoulder surgery; frozen shoulder; shoulder dislocation; after upper extremity fracture; and scapular dyskinesia.

There exist many types of shoulder orthotics in the marketplace, and they all have essentially one underlying theme in common: they provide the support and stability your shoulder needs to heal after an injury or surgery. Such braces are typically designed to limit motion, which helps reduce pain from exaggerated movement following injury or surgery. Also, by keeping the shoulder joint in a secure position these braces help protect against potential re-injury to the actual surgical repair performed on the shoulder joint.

Shoulder stabilization braces (or shoulder immobilization braces) are one type of shoulder orthotic. Shoulder stabilization braces are designed to provide shoulder immobilization and controlled range of motion for glenohumeral dislocations/subluxations, rotator cuff tears and acromioclavicular separations following surgery. They are designed to protect and stabilize the shoulder post-injury and post-operatively. They are not, however, suitable or intended to be used during rehab sessions.

Shoulder slings are another type of shoulder orthotic used to support arm after injury or surgery. Shoulder slings may also be used to limit movement to reduce pain and swelling. They are not, however, suitable for use as a rehab brace.

Another type of shoulder orthotic, posture braces (or posture correctors), function by limiting forward shoulder movements and restricting slouching and bending of the spine. Posture braces provide gentle yet firm support that results in a straighter, taller spine. They are not, however designed to and are generally unable to prevent shoulder hiking during rehab movements when patients begin rehabilitation following shoulder injury or surgery. And this is a major problem because limiting a patient's compensational shoulder hiking movement is critical in order to achieve optimal outcomes.

While all of these types of shoulder orthotics play an important role in patient healing, it is clear that they are not rehab braces that can prevent shoulder hiking during rehab activities. Accordingly, there remains a need for a shoulder rehabilitation brace which can aid patients during their rehab exercises by promoting proper trapezius and scapular positioning and preventing shoulder hiking during rehabilitative sessions.

SUMMARY OF THE INVENTION

The present disclosure provides for a shoulder rehabilitation brace, comprising: a shoulder strap defined by a continuous body having an engaging portion and a connector portion; wherein the shoulder strap is configured such that when worn by a user, the shoulder strap encircles the user's torso, the engaging portion is positioned on a target shoulder of the user, and the connector portion is positioned on the side of the user's torso opposite the target shoulder; a thigh strap configured such to be positioned against a user's thigh; and wherein when the shoulder strap is worn by a user and the thigh strap is positioned against a user's thigh on the side of the user the target shoulder, the connector portion is configured to attach to the thigh strap and cause the engaging portion to exert force on the target shoulder which prevents upward motion with the trapezius of the target shoulder.

BRIEF DESCRIPTION OF THE DRAWINGS

FIG. 3 is a front perspective view of a shoulder harness for a shoulder rehabilitation brace built in accordance with a harness embodiment of the present invention.

FIG. 4 is a front perspective view of a stabilization strap for a shoulder rehabilitation brace built in accordance with a harness embodiment of the present invention.

FIG. 5 is a front perspective view of a thigh strap for a shoulder rehabilitation brace built in accordance with a harness embodiment of the present invention.

DETAILED DESCRIPTION OF THE INVENTION

Described herein are embodiments of a shoulder rehabilitation brace that operates to aid patients in rehabilitating their shoulder joint in an anatomically correct manner to optimize outcomes following injury or surgery so as to deliver vastly improved convenience and benefits relative to existing options in the marketplace. When patients engage in shoulder hiking movements during rehabilitation (or rehab) sessions, it negatively impacts their ability to regain proper shoulder joint functionality and strength of shoulder following injury or surgery. But when embodiments of the shoulder rehabilitation brace is worn during shoulder rehab exercises, forces the patient to perform exercises in an anatomically correct manner that will optimize patient's recovery. The shoulder rehabilitation braces are additionally adjustable so that it can correctly fit on all body types.

Figure 1:
FIG. 1 is a front perspective view of a scapular stabilization technique for rehabilitation activities in accordance with the prior art.
Figure 2:
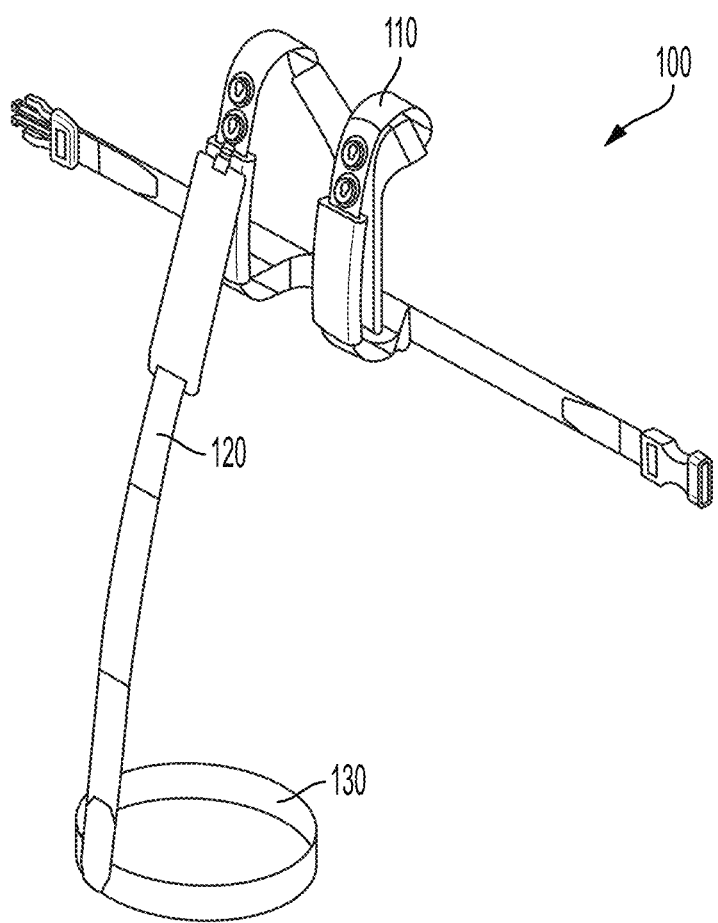
FIG. 2 is a front perspective view of a shoulder rehabilitation brace built in accordance with a harness embodiment of the present invention.

Referring now to the drawings and, in particular, FIG. 1, a common existing technique to reduce shoulder hiking involves a physical therapist T placing their hand on the patient's P trapezius area during in-clinic shoulder rehab sessions. When the patient is at home and trying to do the adjunct home-based exercises prescribed by the therapist, however, there is often no one there to manually "hold down" the trapezius area in order to prevent patient from engaging in the act of shoulder hiking. This unfortunately results in many patients, despite their best efforts, failing to regain full range of motion and strength and even possibly requiring additional surgery to resolve their shoulder problems due to their inability to rehab properly.

Referring now to FIGS. 2, 3, 4, and 5, a harness embodiment of a shoulder rehabilitation brace 100 is shown having a shoulder harness 110, a stabilization strap 120, and a thigh strap 130. When worn by a user, these components work together to emulate the same "hand on trapezius area" function that a therapist manually applies to patient in-clinic. This means users can rehab at any time and do so in an anatomically correct manner as the trapezius is locked down in order to prevent substantial upward shoulder shrug movements (i.e., shoulder hiking) as well as to promote retraction of the shoulder blades in the mid-back area of the trapezius.

The shoulder harness 110 includes of a padded back panel 111, shoulder straps 112, a chest strap 113, and a waist buckle component 114 having two parts that are mechanically attached (by sewing or otherwise) to the opposite ends of the chest strap 113. The shoulder harness 110 additionally includes strap connector receivers in the form of two quick release female connectors 115 positioned on each shoulder strap 112, as well as a protective pad 116 below the female connectors 115 on each of the shoulder straps 112 to prevent shoulder straps 112 from cutting into the skin or causing discomfort. To facilitate adjustments to the circumference of the shoulder harness 110 and accommodate larger patients by increasing length of strapping system, a length adjustment mechanism 117 may be integrated into the chest strap 113.

The length adjustment mechanism 117 may be embodied as a discrete Y tab adjustor (or the hook aspect of another hook and loop fastener material). The length adjustment mechanism 117 may operate with adjustment buckles built into the waist buckle component 114, allowing the length adjustment mechanism 117 to be pulled further away from the ends of the chest strap 113, causing chest strap 113 material to pull through the adjustment buckles built into the waist buckle component 114 (reducing the length of the chest strap 113) and then removably attached to the chest strap 113 at that location.

To put on the shoulder harness 110, a user may place the shoulder harness 110 onto their upper torso (as one does when placing a backpack on themselves), with the back panel 111 against their back, the shoulder straps 112 going over their shoulders, the portion of the shoulder straps 112 containing the female connectors 115 in front of their shoulders, and the two ends of the chest strap 113 hanging from the bottom of the back panel 111. The user then pulls the ends of the chest strap 113 around their body so that the two waist buckle components 114 can connect in front of the user's body fastens the waist buckle components 114 together and adjusts the length adjustment mechanism 117. During this process, the user pulls on the chest strap 113 to tighten it as much as possible so that the shoulder harness 110 will cradle their body. Advantageously, doing this will help keep their shoulder blades in a retracted position because the tighter the shoulder harness 110 cradles the body, the more it retracts the shoulder blades.

With the chest strap 113 tightened and fastened, it causes the shoulder straps 112 to exert force on the user's shoulders to secure the shoulder blades in a retracted position. This occurs due to the counter-pressure the "X" crisscross design of the back panel 111 applies on the shoulder blades as they retract/compress toward the spine. To explain, when a user pulls outwardly 118 on the ends of the chest strap 113, the shoulder straps 112 tighten due to the fact that they are attach to one another. Particularly, the left shoulder strap 112 is tightened by pulling the right end of the chest strap 113 and the right shoulder strap 112 is tightened by pulling the left end of the chest strap 113.

Alternatively, the user may connect the ends of the chest straps 113 together via the waist buckle components 114 after proper shoulder blade retraction tension is achieved.

The stabilization strap 120 is operative to couple the shoulder harness 110 and the thigh strap 130. The stabilization strap 120 include an elongated body 121, a harness connector in the form of a quick release clip segment 122 positioned at the top end of the elongated body 121, a padded tensioner housing 123 positioned adjacent to a top end of the elongated body 121, and a fastening portion 124 which defines the bottom end of the elongated body 121. The quick release clip segment 122 is defined by a corresponding male fastener segment for the female connectors 115, and may be embodied as a stud, hook, or snap fastener style connector (with the female connectors 115 being a corresponding socket aspect thereof) that can be inserted into and releasably connect to the female connectors 115 on the shoulder harness 110. The tensioner housing 123 houses a strap length adjustment mechanism defined as a cable ratchet system and includes a tension adjustment knob 125 for adjusting the tension applied by the cable ratchet system (as discussed below). The fastening portion 124 may be defined by a Y Tab fastener (or the hook aspect of another hook and loop fastener material). The cable ratchet system is positioned between the quick release clip segment 122 and the fastening portion 124 and is used to selectively create tension in the stabilization strap 120 by tightening the cables in the cable ratchet system so as to limit undesirable shoulder hiking motions.

The cable ratchet system may operate with an extension segment 121a of the elongated body 121. In some embodiments, the elongated body 121 may extend from the bottom end to the tensioner housing 123, with the extension segment 121a being the portion of the stabilization strap that extends from the tensioner housing 123 to the top end (with the quick release clip segment 122 attached to the extension segment 121a), with the cable ratchet system operative to shorten or lengthen the extension segment 121a so as to extend or retract the length of the stabilization strap 120.

In some embodiments, the elongated body 121 may extend for the full length of the stabilization strap 120, with the extension segment 121a simply being a portion of the elongated body 121. In such an embodiment, the cable ratchet system may operate to constrict or bunch up a portion of the elongated body 121 in the tensioner housing 123 to lengthen or shorten the amount of the elongated body 121 that extends out of the tensioner housing 123 as the extension segment 121a.

The quick release clip segment 122 can be attached to either female connector 115 on the shoulder harness 110. On any given shoulder strap 112, the upper female connector 115 may used when user rehabs in a seated position and the lower female connector 115 is used when user rehabs in a standing position. After stabilization strap 120 is connected to one of the female connector 115, the user may then attach the bottom end of the stabilization strap 120 the thigh strap 130 as discussed below.

In order to properly fit the user, prior to using this brace, the bottom end of the stabilization strap 120 may be cut in length to properly account for user's height. Once the extra length from the bottom end of the stabilization strap 120 is cut and properly sized for patient then the fastening portion 124 is placed at bottom end of the stabilization strap 120. Then, the fastening portion 124 is secured onto thigh strap 130. Once fitted for proper user length, the user will use the cable ratchet system to create the proper amount of tension required to eliminate shoulder hiking during their rehab sessions.

The thigh strap 130 is defined by a circular strap member that is sized to encircle and otherwise operative to be fastened around the user's upper thigh. The thigh strap 130 has a loop adjustment mechanism 131 that allows for adjustment to its circumference in order to ensure proper patient fitting. The loop adjustment mechanism 131 may be embodied as a buckle.

The shoulder rehabilitation brace 100 allows a user to perform exercises while seated or standing depending how the user connects the stabilization strap 120 to the shoulder harness 110. The manner in which the stabilization strap 120 is connected to the shoulder harness 110 is illustrated in FIGS. 6, 7, and 8.

Figure 6:
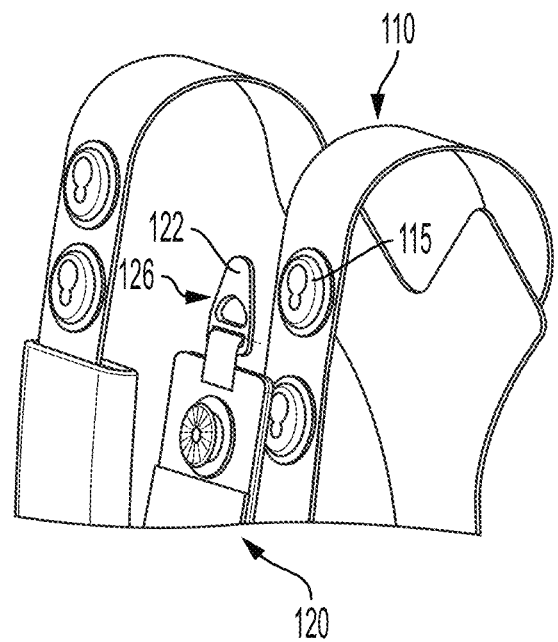
FIG. 6 is a partial side perspective view of a shoulder rehabilitation brace built in accordance with a harness embodiment of the present invention, shown with the stabilization strap being positioned to attach to the shoulder harness.
Figure 7:
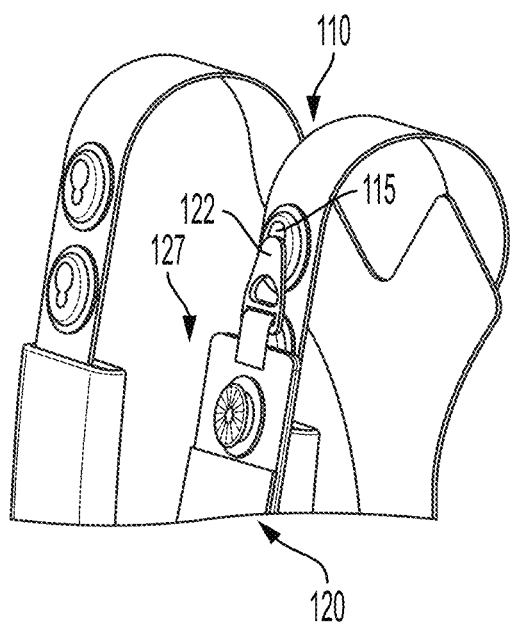
FIG. 7 is a partial side perspective view of a shoulder rehabilitation brace built in accordance with a harness embodiment of the present invention, shown with the stabilization strap being attached to the shoulder harness.

Referring now to FIGS. 6 and 7, to attach the stabilization strap 120 to the shoulder harness 110, the quick release clip segment 122 must be aligned with one of the female connectors 115. As mentioned above, the upper female connector 115 is for use when the user is seated and the lower female connector 115 is for use when the user is standing. As soon as the stud from the quick release clip segment 122 from the stabilization strap 120 is pushed in a insertion direction 126 into the wide portion of the socket of the female connector 115, the user pulls in the securing direction 127 to move the stud into the narrower portion of the socket of the female connector 115. The user may hear an audible click once attachment is successful.

Figure 8:
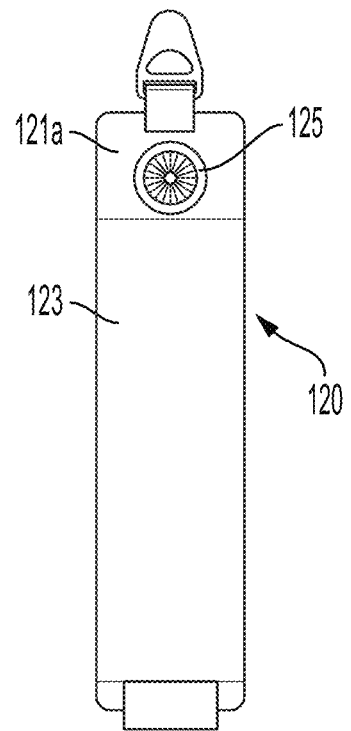
FIG. 8 is a partial front elevational view of a stabilization strap for a shoulder rehabilitation brace built in accordance with a harness embodiment of the present invention, shown with its tension being adjusted.

Referring now to FIG. 8, to adjust how much of the extension segment 121a extends from the tensioner housing 123 (and thus length of the stabilization strap 120), a user may rotate the tension adjustment knob 125 to activate the cable ratchet system and lengthens or shortens the extension segment 121a depending on the direction which the tension adjustment knob 125 is rotated.

Figure 9:
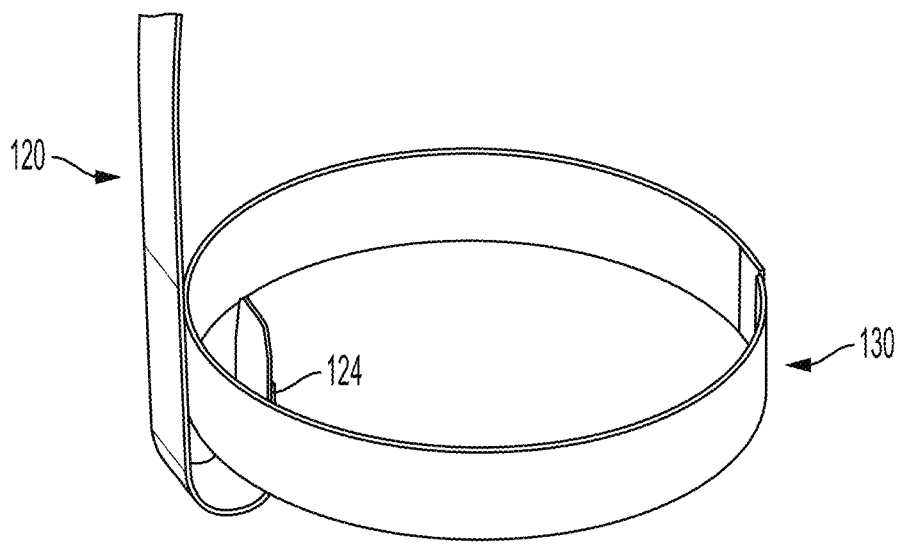
FIG. 9 is a partial side perspective view of a shoulder rehabilitation brace built in accordance with a harness embodiment of the present invention, shown with the stabilization strap being positioned to attach to the thigh harness.
Figure 10:
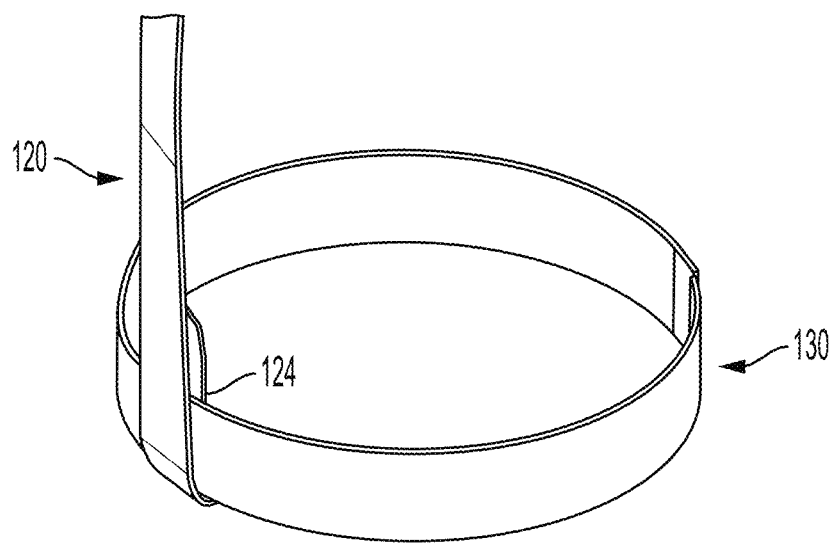
FIG. 10 is a partial side perspective view of a shoulder rehabilitation brace built in accordance with a harness embodiment of the present invention, shown with the stabilization strap attached to the thigh harness.
Figure 11:
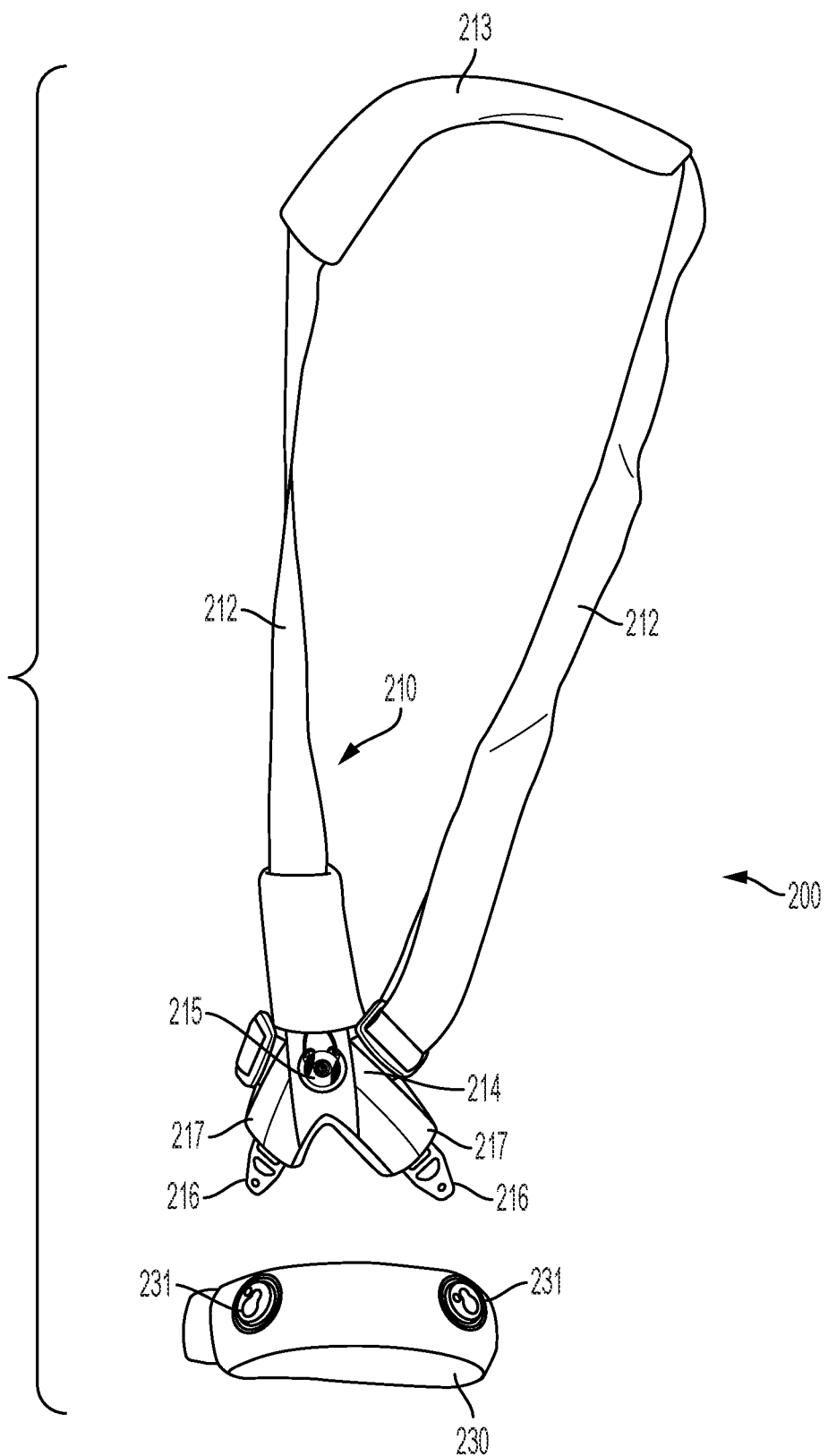
FIG. 11 is a front perspective view of a shoulder rehabilitation brace built in accordance with a strap embodiment of the present invention, shown with the components not connected to one another.
Figure 12:
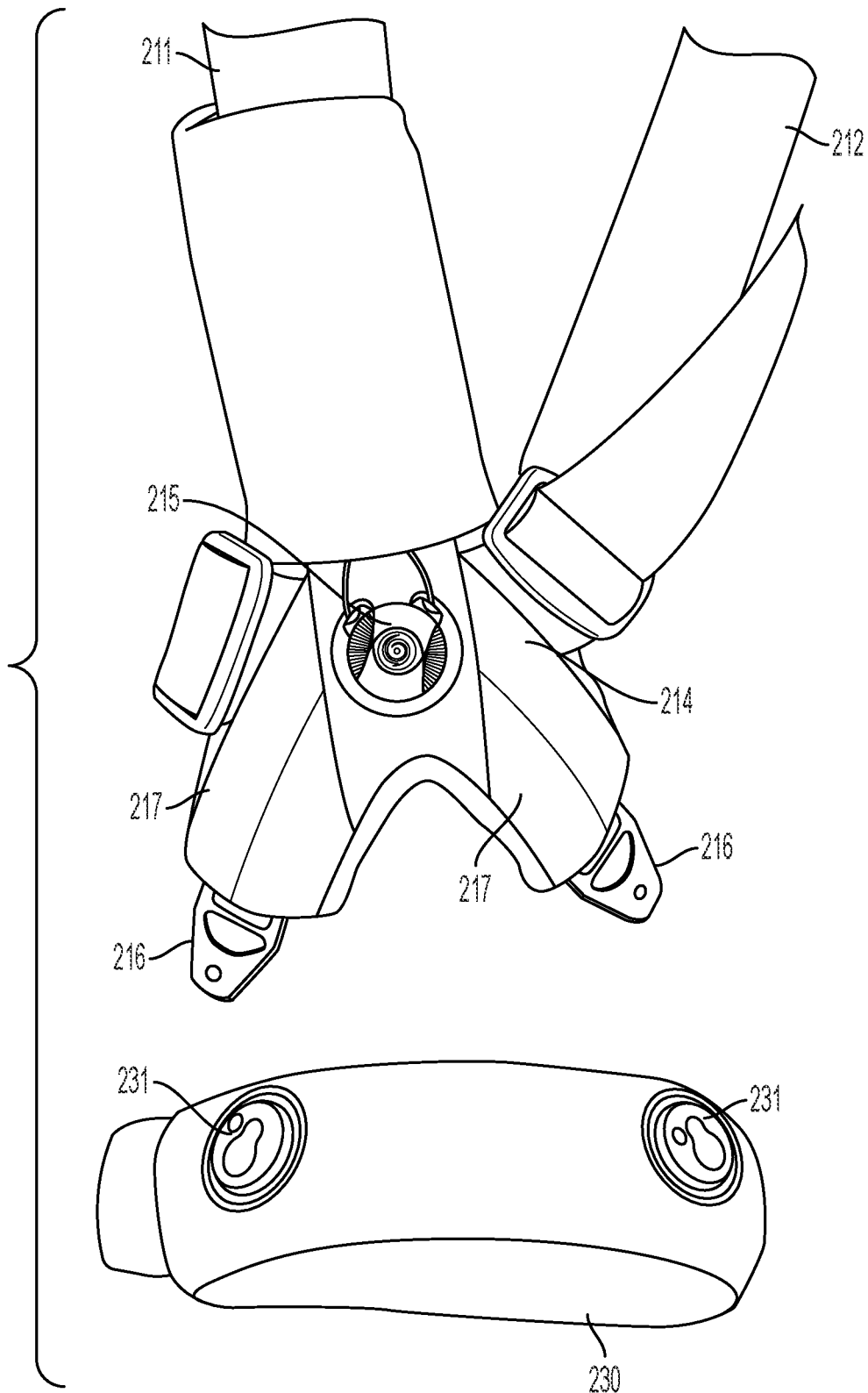
FIG. 12 is a partial front perspective view of a shoulder rehabilitation brace built in accordance with a strap embodiment of the present invention, shown with the components not connected to one another.
Figure 13:
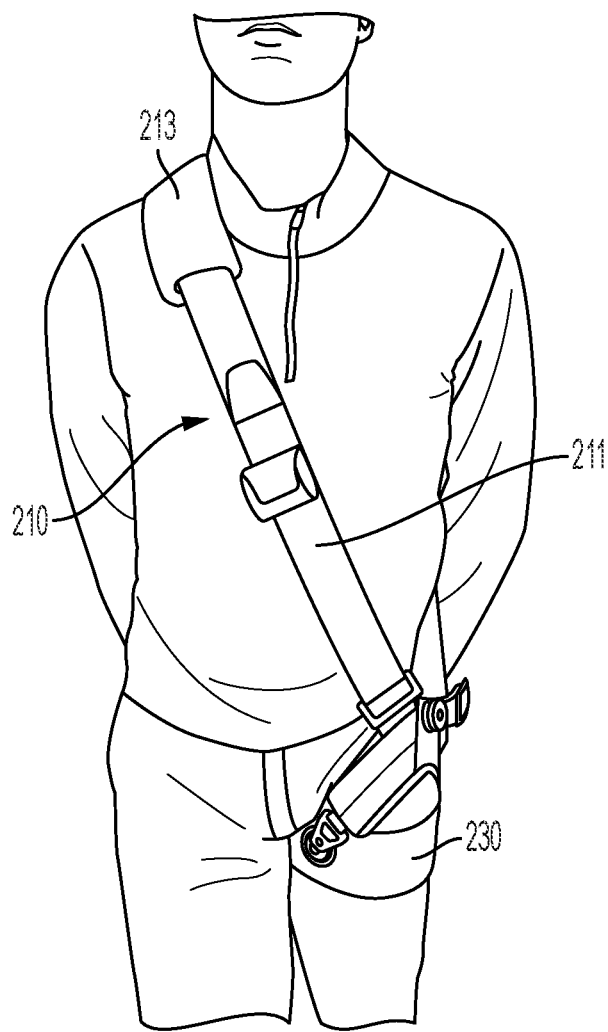
FIG. 13 is a front perspective view of a shoulder rehabilitation brace built in accordance with a strap embodiment of the present invention, shown in place on a user with the components connected to one another.

Referring now to FIGS. 9 and 10, the stabilization strap 120 may be secured onto the thigh strap 130 via the fastening portion 124 being wrapped around the thigh strap 130 and fastened to the interior side of the thigh strap 130 and/or the stabilization strap 120. When the stabilization strap 120 is connected to shoulder harness 110, then fastened onto the thigh strap 130, the shoulder rehabilitation brace 100 prevents shoulder hiking in part because the thigh strap 130 acts as an anchor which assists the shoulder harness 110 in preventing upward shoulder hiking.

It is contemplated that the strap aspects of the shoulder harness, the thigh strap, and the stabilization strap may be formed of nylon with at least a portion having a surface that is analogous to a loop component of a hook and loop fastener.

Referring now to FIGS. 11, 12, 13, and 14, a strap embodiment of a shoulder rehabilitation brace 200 is shown having a shoulder strap 210 and a thigh strap 230. When worn by a user, these components work together to emulate the same "hand on trapezius area" function that a therapist manually applies to patient in-clinic, with the shoulder strap 210 acting directly on the shoulder and the thigh strap 230 acting as an anchor which assists the shoulder strap 210 in preventing upward shoulder hiking. This means users can rehab at any time and do so in an anatomically correct manner as the trapezius is locked down in order to prevent substantial upward shoulder shrug movements (i.e., shoulder hiking) as well as to promote retraction of the shoulder blades in the mid-back area of the trapezius.

The shoulder strap 210 includes a front portion 211, a back portion 212, a engaging portion 213, and a connector portion 214. The engaging portion 213 is positioned between the front portion 211 and the back portion 212 and is the portion of the shoulder strap 210 which will engage and exert force on the user's shoulder when the shoulder rehabilitation brace 200 is in use. In this regard, the engaging portion 213 may include a padded section integral therewith. The front portion 211, engaging portion 213, and the back portion 212 together form a continuous strap body that loops out of at one end the connector portion 214 at one end and back into the connector portion 214 at the other end. In this way, the shoulder strap 210 is sized to encircle and otherwise operative to be placed around a user's upper body, being positioned over a target shoulder (the shoulder on which the "hand on trapezius area" function is being emulated), across the chest and back, and around the hip opposite the target shoulder.

Figure 14:
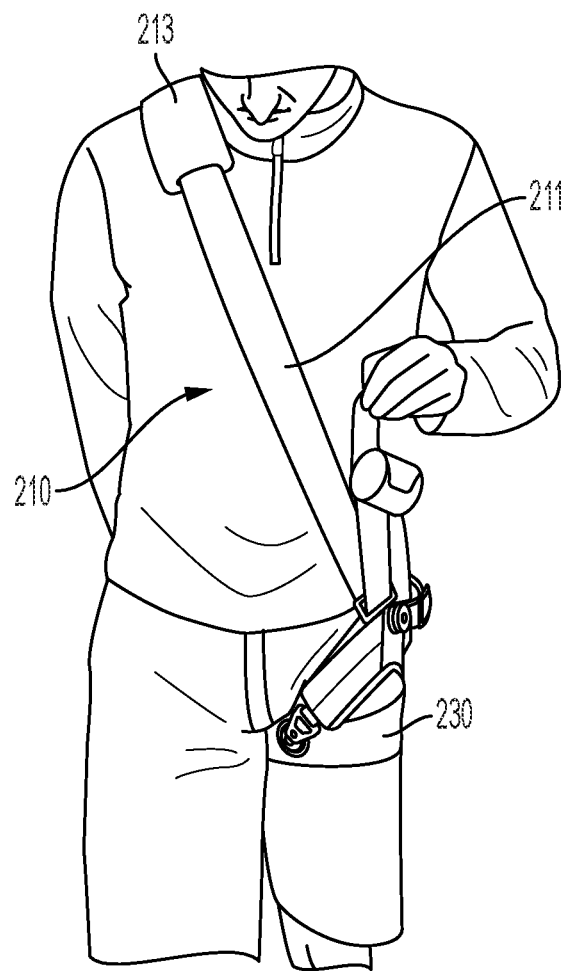
FIG. 14 is a front perspective view of a shoulder rehabilitation brace built in accordance with a strap embodiment of the present invention, shown in place on a user with the components connected to one another and a user adjusting the torso loop adjustment mechanism.

The shoulder strap 210 may include a torso loop adjustment mechanism that allows for adjustment to the length of its loop in order to ensure proper patient fitting around a user's upper body. The torso loop adjustment mechanism may include a buckle integral into the front portion 211 (with part of the front portion inserted into the buckle) so that a user may pull part of the front portion 211 through the buckle to increase or decrease the length of the front portion 211 which extends between the connector portion 214 and the engaging portion 213, all while the shoulder strap 210 is around the user. This action is illustrated in FIG. 14.

The connector portion 214 additionally includes a tensioning actuator 215 and a pair of strap connectors 216. The tensioning actuator 215 is defined in the illustrated embodiment as a rotary knob and may be integral with an internal cable ratchet system running inside the connector portion 214.

The strap connectors 216 each may be positioned on a connector extender 217 that extends from the connector portion 214. One of the connector extenders 217 may extend from the connector portion 214 in the opposite direction as the front portion 211, and the other of the connector extenders 217 may extend from the connector portion 214 in the opposite direction as the back portion 212.

The thigh strap 230 is defined by a strap member that is sized to encircle and otherwise operative to be fastened around a user's upper thigh. When in use, the thigh strap 230 is worn on the thigh that is on the same side as the hip on the user that the shoulder strap 210 goes around, that being the opposite side of the shoulder that the shoulder strap 210 is placed on.

The thigh strap 230 may include a thigh loop adjustment mechanism that allows for adjustment to its circumference in order to ensure proper patient fitting. The loop adjustment mechanism may be embodied as a buckle.

The thigh strap 230 additionally includes a pair of connector receivers 231 positioned on an exterior surface of the thigh strap 230, with the exterior surface of the thigh strap being the surface that is opposite the surface that contacts a user when the thigh strap 230 is being worn. The connector receivers 231 correspond to the strap connectors 216 of the shoulder strap 210 so that together each of the strap connectors 216 may be coupled with one of the connector receivers 231 to form a releasable fastener which operates to selectively attach the shoulder strap 210 to the thigh strap 230.

In this regard, each of the connector receivers 231 may be defined as a quick release female connector that includes a socket and each of the strap connectors 216 may be defined as a quick release male connector that includes a stud, hook, or snap fastener style connector that corresponds to the socket.

The tensioning actuator 215 and cable ratchet system may be employed to create a tension in the shoulder strap 210 that can prevent unwanted movement when the shoulder rehabilitation brace 200 is in place on a user. In some embodiments, the cable ratchet system and the tensioning actuator 215 may be formed from a Boa® fit system.

The tensioning actuator 215 and cable ratchet system together operate by tightening and locking or loosening and locking a set of cables which run between the two strap connectors 216 and connector extender 217 assemblies. This action allows for the selective creation and removal of tension in the shoulder strap 210.

When the cable ratchet system is tensioned, the tensioning may be directed towards the strap connector 216 and connector extender 217 assembly that is opposite the rear portion 212 so that the tensioning primarily occurs on the rear portion 212. It is contemplated, however, that tensioning may be directed toward the rear portion 212 more directly by the cables of the cable ratchet system. In any event, this design optimizes the correct anatomical position needed for patient to rehabilitate their shoulder as it optimally prevents shoulder/scapular hiking and keeps the shoulder blade in retracted position in a manner that helps prevent potential shoulder impingement scenarios.

To wear the shoulder rehabilitation brace 200, a user will first attach the thigh strap 230 to the leg that is opposite to the side of their injured shoulder. The user will then slide the shoulder strap 210 onto the affected shoulder, with the shoulder strap 210 positioned across their torso to that the connector portion 214 is on the hip opposite the injured shoulder. Then, the user will fasten the strap connectors 216 to the connector receivers 231, attaching the shoulder strap 210 to the thigh strap 230. With the shoulder strap 210 attached to the thigh strap 230, the user may adjust the torso loop adjustment mechanism by pulling on the front portion 211. The user may then turn the tensioning actuator 215 until there is sufficient tension is achieved and trapezius is in a locked position.

It is contemplated that as the shoulder strap 210 and the thigh strap each contain two connectors, the shoulder rehabilitation brace 200 may be worn on either shoulder, depending on which side the injury occurred.

Figure 15:
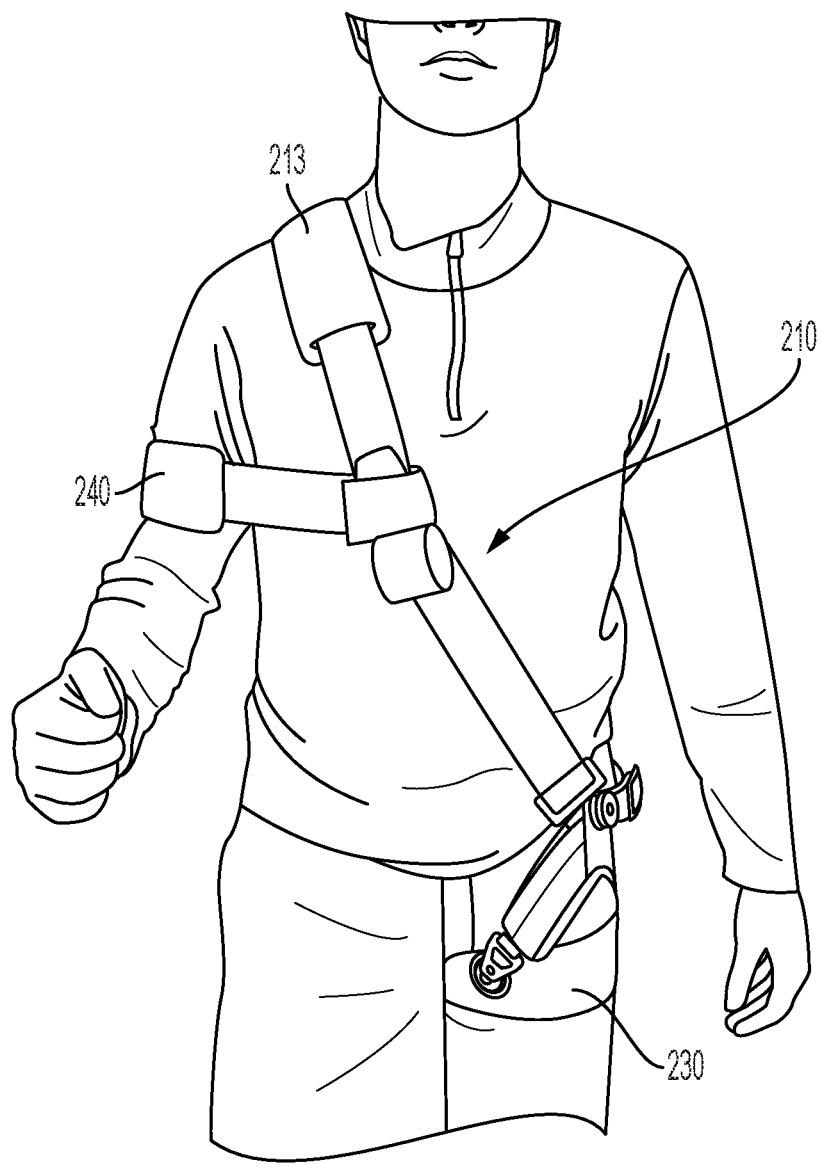
FIG. 15 is a front perspective view of a shoulder rehabilitation brace built in accordance with a plural strap embodiment of the present invention, shown in place on a user with the components connected to one another.

Referring now to FIG. 15, the shoulder rehabilitation brace 200 may be worn with an abduction strap 240. The abduction strap 240 is attachable to the front portion 211 at one end and the back portion 212 at the other end. The abduction strap 240 may be attachable to these portions of the shoulder strap 210 through corresponding portions of a hook and loop fastener system with corresponding portions in place on the shoulder strap 210 and on the ends of the abduction strap 240. When in place, the abduction strap 240 optimizes the performance of rotation exercises by keeping a user's against their body while performing various external and internal rotation exercises.

When in use, embodiments of the shoulder rehabilitation brace help a user regain full range of motion and strength by ensuring that the user performs their rehab exercises in an anatomical correct manner during shoulder rehab sessions. A common movement that people tend to do with their shoulders while rehabbing is called "shoulder/scapular hiking." This occurs when a person shrugs their shoulder upwards in order to reduce the pain while using their shoulders. This can lead to improper mechanics which can lead to poor outcomes and may lead to a secondary surgical procedure such as manipulation under anesthesia ("MUA").

Significantly, embodiments of the shoulder rehabilitation brace eliminate patient cheating during exercise/rehabilitation sessions and prevent a patient from engaging in scapular/shoulder hiking during rehab session. The shoulder rehabilitation brace prevents the user from shrugging their injured shoulder upwards (upward motion with their trapezius). This is done through the combined operation of the shoulder strap, tensioned with the cable ratchet system, and the thigh strap so that the user is unable to shrug their shoulder upwards. This optimizes patient recovery because cheating in the form of shoulder hiking significantly impacts user's ability to rehab correctly. Thus, embodiments of the shoulder rehabilitation brace reduce the likelihood of prolonged rehab sessions and reduces the likelihood of frozen shoulder and secondary surgery such as an MUA or Lysis of Adhesion Surgery due to poor rehab outcomes.

Embodiments of the shoulder rehabilitation brace also keep a user's shoulder blades in a retracted position, namely compressed inward towards the spine, and locks down the top of the trapezius to prevent it from engaging in an upward motion during rehab. When a patient goes thru rehab without properly addressing scapular hiking issues during rehab, it permanently alters proper mechanics. Such an improper alignment leads to long term complications which will limit quality of life and arm functionality and may lead to additional therapy and/or surgery.

In addition, the use of the abduction strap with the shoulder rehabilitation may optimize external rotation exercise. One of the most common and severe injuries to the shoulder is when the rotator cuff is torn. When the rotator cuff is torn, a person must perform external and internal rotation exercises. When doing so, it is important to keep the arm from abduction in order to properly perform these exercises. Advantageously, the abduction strap prevents arm/elbow from flying away from the body, thus it keeps it in a locked position so that exercises can be properly performed The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. A shoulder rehabilitation brace, comprising:
   a shoulder strap defined by a continuous body having a connector portion, wherein the shoulder strap is configured such that when worn by a user, the shoulder strap encircles the user's torso and engages a target shoulder of the user, with the connector portion is positioned on the side of the user's torso opposite the target shoulder;
   a plurality of strap connectors integral with said connector portion, with a first strap connector among the plurality of strap connectors extending out of the connector portion at a first angular orientation and a second strap connector among the plurality of strap connectors extending out of the connector portion at a second angular orientation that is an intersecting orientation relative to the first angular orientation;
   a discrete thigh strap configured to be positioned around a user's thigh, wherein the first strap connector and the second strap connector, respectively, are each configured to releasably attach to the thigh strap at discrete locations; and wherein when the shoulder strap is worn by a user, the thigh strap is positioned against a user's thigh on the opposite side of the user's target shoulder, and the first strap connector and the second strap connector are each attached to the thigh strap, the shoulder strap is positioned to prevent shoulder hiking in the target shoulder.

2. The shoulder rehabilitation brace of claim 1, wherein the shoulder strap additionally includes an engaging portion, a front portion and a back portion, with the shoulder strap is configured such that the front portion extends between the engaging portion and the connector portion in front of the target shoulder when the shoulder strap is worn by a user and the shoulder strap is configured such that the back portion extends between the engaging portion and the connector portion behind the target shoulder when the shoulder strap is worn by a user.

3. The shoulder rehabilitation brace of claim 2, wherein the engaging portion includes a padded section.

4. The shoulder rehabilitation brace of claim 2, wherein the second strap connector extends out of the connector portion at an intersecting angle relative to the orientation of the front portion as it extends into the connector portion as well as to the orientation of the first strap connector.

5. The shoulder rehabilitation brace of claim 1, wherein the shoulder strap includes a torso loop adjustment mechanism.

6. The shoulder rehabilitation brace of claim 5, wherein the torso loop adjustment mechanism is integral with the front portion.

7. The shoulder rehabilitation brace of claim 1, wherein the connector portion includes a tensioning actuator configured to selectively create and remove tension in the shoulder strap.

8. The shoulder rehabilitation brace of claim 7, wherein the tensioning actuator is configured to selectively create and remove tension in the back portion.

9. The shoulder rehabilitation brace of claim 1, additionally comprising an abduction strap configured to attach in two discrete locations to the shoulder strap and, when the shoulder strap is worn by a user and the abduction strap is attached to the shoulder strap, encircle the arm underneath the target shoulder and fix the encircled arm against the user's torso.

10. A shoulder rehabilitation brace, comprising:
a shoulder strap defined by a continuous body having a front portion, an engaging portion, a back portion, and a connector portion;
wherein the shoulder strap is configured such that when worn by a user, the shoulder strap encircles the user's torso with the engaging portion positioned on a target shoulder of the user, the connector portion positioned on the side of the user's torso opposite the target shoulder, the front portion extending between the engaging portion and the connector portion in front of the target shoulder, and the back portion extending between the engaging portion and the connector portion behind the target shoulder;
a plurality of strap connectors integral with said connector portion, with a first strap connector among the plurality of strap connectors extending out of the connector portion at an intersecting angle relative to the orientation of the front portion as it extends into the connector portion and a second strap connector among the plurality of strap connectors extending out of the connector portion at an intersecting angle relative to the orientation of the first strap connector;

a discrete thigh strap configured such to be positioned around a user's thigh, wherein the first strap connector and the second strap connector, respectively, are each configured to releasably attach to the thigh strap at discrete locations; and
wherein when the shoulder strap is worn by a user, the thigh strap is positioned against a user's thigh on the opposite side of the user's target shoulder, and the first strap connector and the second strap connector are each attached to the thigh strap, the shoulder strap is positioned to prevent shoulder hiking in the target shoulder.

11. The shoulder rehabilitation brace of claim 10, wherein the shoulder strap includes a torso loop adjustment mechanism.

12. The shoulder rehabilitation brace of claim 11, wherein the torso loop adjustment mechanism is integral with the front portion.

13. The shoulder rehabilitation brace of claim 10, wherein the connector portion includes a tensioning actuator configured to selectively create and remove tension in the shoulder strap.

14. The shoulder rehabilitation brace of claim 10, additionally comprising an abduction strap configured to attach in two discrete locations to the shoulder strap and, when the shoulder strap is worn by a user and the abduction strap is attached to the shoulder strap, encircle the arm underneath the target shoulder and fix the encircled arm against the user's torso.

15. The shoulder rehabilitation brace of claim 10, wherein the engaging portion includes a padded section.

16. The shoulder rehabilitation brace of claim 10, wherein the second strap connector extends out of the connector portion at an intersecting angle relative to the orientation of the front portion as it extends into the connector portion as well as to the orientation of the first strap connector.

17. A shoulder rehabilitation brace, comprising:
a shoulder strap defined by a continuous body having a front portion, an engaging portion, a back portion, and a connector portion;
wherein the shoulder strap is configured such that when worn by a user, the shoulder strap encircles the user's torso with the engaging portion positioned on a target shoulder of the user, the connector portion positioned on the side of the user's torso opposite the target shoulder, the front portion extending between the engaging portion and the connector portion in front of the target shoulder, and the back portion extending between the engaging portion and the connector portion behind the target shoulder;
a discrete thigh strap configured such to be positioned around a user's thigh, wherein the thigh strap includes a plurality of connector receivers;
a plurality of strap connectors integral with said connector portion, with a first strap connector among the plurality of strap connectors extending out of the connector portion at an intersecting angle relative to the orientation of the front portion as it extends into the connector portion and a second strap connector among the plurality of strap connectors extending out of the connector portion at an intersecting angle relative to the orientation of the back portion as it extends into the connector portion, wherein the first strap connector and the second strap connector, on one hand, and two of the connector receivers among the plurality of connector receivers on the other, together form corresponding portions of two fasteners which can be releasably attached together; and wherein when the shoulder strap is worn by a user, the thigh strap is positioned against a user's thigh on the opposite side of the user's target shoulder, and the first strap connector and the second strap connector, respectively, are attached to two of the connector receives among the plurality of connector receivers, the shoulder strap is positioned to prevent shoulder hiking in the target shoulder.

18. The shoulder rehabilitation brace of claim 17, wherein the connector portion includes a tensioning actuator configured to selectively create and remove tension in the shoulder strap.

19. The shoulder rehabilitation brace of claim 18, wherein:
   the shoulder strap includes a torso loop adjustment mechanism; and
   the tensioning actuator is configured to selectively exert force at a location in between the front strap connector the back strap connector so as to selectively create and remove tension in the back portion.

20. The shoulder rehabilitation brace of claim 19, additionally comprising an abduction strap configured to attach in two discrete locations to the shoulder strap and, when the shoulder strap is worn by a user and the abduction strap is attached to the shoulder strap, encircle the arm underneath the target shoulder and fix the encircled arm against the user's torso.

* * * * *